United States Patent
Koschnick et al.

(10) Patent No.: US 10,111,436 B2
(45) Date of Patent: *Oct. 30, 2018

(54) CONTROL OF AQUATIC WEEDS WITH ENDOTHALL AND ALS-INHIBITING AGENT

(71) Applicant: SePRO Corporation, Carmel, IN (US)

(72) Inventors: Tyler J. Koschnick, Westfield, IN (US); David P. Tarver, Tallahassee, FL (US)

(73) Assignee: SePRO Corporation, Carmel, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/245,154

(22) Filed: Apr. 4, 2014

(65) Prior Publication Data
US 2015/0018213 A1 Jan. 15, 2015

Related U.S. Application Data

(63) Continuation of application No. 12/429,738, filed on Apr. 24, 2009, now Pat. No. 8,716,183.

(60) Provisional application No. 61/048,147, filed on Apr. 25, 2008, provisional application No. 61/148,250, filed on Jan. 29, 2009.

(51) Int. Cl.
| | | |
|---|---|---|
| *A01N 43/90* | (2006.01) | |
| *A01N 43/54* | (2006.01) | |
| *A01N 47/36* | (2006.01) | |
| *A01N 43/50* | (2006.01) | |
| *B65D 81/32* | (2006.01) | |

(52) U.S. Cl.
CPC .......... *A01N 43/90* (2013.01); *A01N 43/50* (2013.01); *A01N 43/54* (2013.01); *A01N 47/36* (2013.01); *B65D 81/32* (2013.01)

(58) Field of Classification Search
CPC ........ A01N 43/90; A01N 47/36; A01N 43/50; A01N 43/54; A01N 39/02; B65D 81/32
See application file for complete search history.

(56) References Cited

U.S. PATENT DOCUMENTS 8,716,183 B2 * 5/2014 Koschnick ............. A01N 43/90
504/118

OTHER PUBLICATIONS

Borger, J.A., Annual Bluegrass Control and More, 2005, Proceedings of the Fifty-ninth Annual Meeting of the Northeastern Weed Science Society, 3 pages.*
Anonymous, Penoxsulam and its Use as a Herbicide in Mixtures for use in Rice, Wheat, Barley, Oats, Sorghum, Corn, Maize, IVM, Rangeland, Pastures, Grasslands, Fallowland, Turf and Aquatics, 2005, IP.com, Technical Disclosure, 15 pages.*
Aquathol K, Aquatic Herbicide, 2005, Product Sheet, Cerexagri, Inc., 11 pages.*
Koschnick, T., Effects of Three ALS-Inhibitors on Five Emergent Native Plant Species in Florida, Jan. 2007, Journal of Aquatic Plant Management, vol. 45, pp. 47-51.*
Skogerboe, J., Combining Endothall with Other Herbicides for Improved Control of Hydrill—A Field Demonstration, Aug. 2004, APCRP, ERDC/TN APCRP-CC-04, pp. 1-7.

* cited by examiner

*Primary Examiner* — John D Pak
*Assistant Examiner* — Andriae M Holt
(74) *Attorney, Agent, or Firm* — Woodard, Emhardt, Moriarty, McNett & Henry LLP

(57) ABSTRACT

Described are preferred methods and compositions for controlling aquatic weeds that involve the use of an ALS-inhibiting herbicidal agent such as penoxsulam in combination with endothall. Preferred herbicidal combinations allow for enhanced control when treating a body of water to control a target weed population, such as *hydrilla*.

15 Claims, 7 Drawing Sheets

CONTROL OF AQUATIC WEEDS WITH ENDOTHALL AND ALS-INHIBITING AGENT

REFERENCE TO RELATED APPLICATION

The present application is a continuation of U.S. application Ser. No. 12/429,738 filed Apr. 24, 2009, entitled CONTROL OF AQUATIC WEEDS WITH ENDOTHALL AND ALS-INHIBITING AGENT, which claims the benefit of U.S. Provisional Patent Application No. 61/048,147 filed Apr. 25, 2008, entitled CONTROL OF AQUATIC WEEDS WITH PENOXSULAM AND ENDOTHALL, and of U.S. Provisional Patent Application No. 61/148,250 filed Jan. 29, 2009, entitled CONTROL OF AQUATIC WEEDS WITH ENDOTHALL AND ALS-INHIBITING AGENT, each of which is hereby incorporated herein by reference in its entirety.

BACKGROUND

The present invention related generally to methods and compositions for controlling aquatic weeds, and certain particular embodiments, methods and compositions for selectively controlling weeds such as *hydrilla* or watermilfoil utilizing a combination including penoxsulam or another ALS inhibitor herbicide and endothall.

As further background, aquatic plants very commonly arise as undesired weeds in waters and wetlands in the United States of America and elsewhere. Two such exotic weeds are *hydrilla* and watermilfoil, including Eurasian watermilfoil, which present problems in ponds, lakes, and other water bodies. The treatment of such bodies of water to eliminate or control the undesired or exotic aquatic weeds is often complicated by the fact that the agent used to control the undesired weed also can detrimentally affect the health of other, desirable or native plant life within the water body. Aquatic herbicides need to be in contact with submersed plants for a period of time (exposure time), which is dependent on the individual agent and the concentration at which it is used. Additionally, specific herbicides can require long exposures (months) to control certain plants in water, which can also cause increased detriment to non-target species. Furthermore, long exposures can be difficult to maintain in a fluid environment. Insufficient exposure can lead to poor efficacy or failed treatments. Thus, methods or techniques to reduce exposure times and/or reduce the concentrations of agents used to control submersed weeds could benefit efficacy and/or selectivity. Also, relying on a single herbicide mode of action can enhance the risk of selecting a resistant plant biotype to that particular agent. Thus, treatment regimens that are more selective for the undesired plant species, minimize potential for resistance development, and reduce exposure times are needed.

The efficacy and application rate of herbicidal agents against the target aquatic weeds depends on several factors, including, the specific formulation, the plant type, climatic conditions, water and sediment conditions in the water body, herbicide exposure time, and the like. At times, an inability to control an undesired plant can be eliminated simply by increasing the rate of application for a particular herbicidal agent. However, this is not always the case, and higher rates of application can exacerbate undesired affects on beneficial plants and aquatic organisms, and may not adequately compensate for insufficient exposure with the targeted plant.

One possible way to improve aquatic weed control is to combine two or more active compounds as part of a treatment program. However, the use of two or more active compounds often fails due to physical or biological incompatibility, lack of stability in co-formulation, decomposition of the compounds, antagonistic effects between the compounds, cost, and/or other factors.

In view of the background in aquatic weed control, the discovery of enhanced or alternative methods and compositions for the control of aquatic weeds has been a difficult endeavor. Serious needs thus remain.

SUMMARY

It has been discovered that aquatic weeds such as *hydrilla* can be effectively controlled by combinations including an ALS-inhibiting herbicide, such as penoxsulam, and endothall. Aspects of the present invention therefore relate to methods for treating water bodies to control undesired aquatic weeds with combinations including these active agents, to compositions including such combinations, and to methods for preparing herbicidal combination compositions which involve mixing such active agents to provide a combination. Still further inventive embodiments, as well as features and advantages thereof, will be apparent from the descriptions herein.

DETAILED DESCRIPTION

For the purposes of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

As discussed above, aspects of the present invention relates to methods and compositions involving the use of penoxsulam or another ALS inhibitor herbicide in combination with endothall for controlling aquatic weeds, and especially *hydrilla*. Such combinations desirably: enable the use of lower levels of each herbicidal agent as compared to that which would have to be used with each agent individually; enable the use of sub-lethal levels of each herbicidal agent (if used individually); enable a reduction in the total amount of herbicide needed for control; enable a reduction in the total exposure time needed for control; exhibit an activity that is greater than the individual agents when used alone, more desirably a synergistic or at least additive effect; enhance the level of control for the target aquatic weed population; and/or enhance the selectivity for the target aquatic weed population. As well, the use of such herbicidal agent combinations may enhance the treatment of aquatic weed biotypes that have developed resistance to at least one of the agents included, and may benefit long term weed control by inhibiting the development of additional resistant biotypes.

The chemical penoxsulam (2-(2,2-difluoroethoxy)-6-trifluoromethyl-N-(5,8-dimethoxy[1,2,4]triazolo[1,5c]pyrimidin-2-yl)benzenesulfonamide)) is an acetolactate synthase (ALS) or acetohydroxy acid synthase (AHAS) inhibitor. These agents inhibit the ALS or AHAS enzyme, which leads to the depletion of key amino acids that are necessary for protein synthesis and plant growth (referred to as ALS-inhibiting, ALS-inhibitors, ALS compounds and the like). The following agents, although not limited to, also belong to this class: bensulfuron-methyl, bispyribac sodium, and imazamox.

The chemical endothall ((3,6-endoxohexahydrophthalic acid), also known as (7-oxabicyclo[2.2.1]heptane-2,3-dicarboxylic acid)) is a contact herbicide. It is a membrane-active herbicide that disrupts cell function and chemical gradients, and inhibits protein synthesis in plant metabolism; its exact mechanism of action is unknown. Currently, endothall is commercially available for aquatic use as its dipotassium and as its mono (N,N-dimethylalkylamine: alkyl groups as derived from coconut oil) salts of endothall (sold under such tradenames including Aquathol and Hydrothol).

It will be understood that herbicidal compounds such as those identified herein by generic name are often available as a parent compound or as an active herbicide derivative such as a salt or ester. Accordingly, all such herbicidal active derivatives are intended to be encompassed by use of the generic name for the chemical, unless otherwise specified.

In accordance with certain embodiments of the invention, methods for the control of *hydrilla* or other undesirable aquatic weeds include the application of a combination including penoxsulam and endothall. As to amounts, these agents will be included in a combination that is effective to achieve control of the aquatic weed in question. Typically, for penoxsulam, such amounts will be in the range of about 1 to about 50 parts per billon (ppb), or about 2.5 to about 50 ppb, more typically in the range of about 2 to about 30 ppb or about 5 to about 40 ppb in certain embodiments; and for endothall, such amounts will be in the range of about 0.05 to about 3.5 parts per million (ppm acid equivalence or a.e.) or about 1 to about 3.5 ppm a.e., more typically in the range of about 0.1 to 3.0 ppm a.e. and still more typically in the range of about 0.25 to 2.0 ppm a.e. It has been discovered that endothall, when used in combination with an ALS inhibitor, can be used at low levels while nonetheless achieving good control of a target weed, such as *hydrilla*. In certain preferred embodiments of the invention, the endothall agent will thus be used in the combination at a low level, such as about 1.4 ppm a.e. or less, more preferably about 1 ppm a.e. or less, for example in certain embodiments in a range of about 0.5 to 1 ppm a.e. It has also been discovered that such herbicidal combinations can be used together without having the herbicidal agents antagonize one another, and in fact while achieving a surprisingly rapid control of the target weeds with at least an additive effect.

Methods and compositions of the invention may be used in the complete or partial control of many noxious aquatic weeds. These include, for example, common duckweed (*Lemna minor*), of the emersed plants spatterdock (*Nuphar luteum*) and water-lily (*Nymphaea* spp.), of the submersed plants bladderwart (*Utricularia* spp.), common coontail (*Ceratophyllum demersum*), common elodea (*Elodea canadensis*), Brazilian elodea (*Egeria densa*) fanwort (*Cabomba caroliniana*), hydrilla (*Hydrilla verticillata*), naiad (*Najas* spp.), pondweed (*Potamogeton* spp.) including curlyleaf pondweed (*Potamogeton crispus*), watermilfoil (*Myriophyllum* spp.) including Eurasian watermilfoil (*Myriophyllum spicatum*), floating plants including common watermeal (*Wolffia columbiana*) and salvinia (*Salvinia* spp.), emersed plants including alligatorweed (*Alternanthera philoxeroides*), American lotus (*Nelumbo lutea*), cattail (*Typha* spp.), creeping waterprimrose (*Ludwigia peploides*), parrotfeather (*Myriophyllum aquaticum*), smartweed (*Polygonaum* spp.), spikerush (*Eleocharis* spp.), waterpurslane (*Ludwigia palustris*), and watershield (*Brasenia schreberi*), of the submersed plants Illinois pondweed (*Potamogeton illinoensis*), limnophila (*Limnophila sessiliflora*), tapegrass or American eelgrass (*Vallisneria americana*), and variable leaf watermilfoil (*Myriophyllum heterophyllum*), and the shoreline grasses barnyardgrass (*Echinochloa crusgalli*), and southern watergrass (*Hydrochloa caroliniensis*). Particularly preferred plant types for control in accordance with the invention include *hydrilla*, curlyleaf pondweed, egeria, and watermilfoil.

For use together, it is not necessary that the penoxsulam or other ALS-inhibiting agent and endothall be applied in a physically combined form, or even at the same time. The combination effect results so long as the two or more herbicides are present in contact with the plant at the same time, regardless of when they were applied. Thus, for instance a physical combination of the two or more herbicides could be applied, or one or some could be applied earlier than the other(s). In certain embodiments, the herbicides will be applied within 1 to 7 days of each other, although other embodiments may be used. Typically, the ALS-inhibitor/endothall combination will be applied within about 30 days of each other, or more typically within 1 to 21 days of each other or simultaneously. However, the herbicides could be applied within about 30 to 90 days of each other, or less, when one agent is applied in the presence of or following an exposure to the other agent to reduce exposure time, inhibit potential for plant recovery, or enhance efficacy. Further, it will be understood that the penoxsulam or other ALS-inhibiting herbicide and endothall can be used in combination with one or more additional herbicidal agents, for example one or more additional ALS inhibitor herbicidal agents and/or one or more additional contact type herbicidal agents, or penoxsulam could be replaced with another ALS-inhibiting herbicide agent for aquatic use, such as bispyribac-sodium, imazamox, or bensulfuron-methyl.

In certain embodiments, a method of controlling aquatic weeds involves the use of a combination including bispyribac-sodium and endothall. In such embodiments, the endothall can be used used at a level in the range of about 0.1 to 3.5 ppm a.e., in certain embodiments at a level of less than about 1.4 ppm a.e., and typically at a level in the range of about 0.35 to about 1 ppm a.e., more preferably about 0.5 to about 1 ppm a.e.; and, the bispyribac-sodium is used at a level less than about 0.5 ppm, and typically at a level in the range of about 0.01 to about 0.25 ppm, more preferably about 0.02 to about 0.1 ppm.

In other inventive embodiments, a method of controlling aquatic weeds involves the use of a combination including imazamox and endothall. In such embodiments, the endothall can be used at a level in the range of about 0.1 to 3.5 ppm a.e., in certain embodiments at a level of less than about 1.4 ppm a.e., and typically at a level in the range of about 0.35 to about 1 ppm a.e., more preferably about 0.5 to about 1 ppm a.e.; and, the imazamox is used at a level less than about 0.2 ppm, and typically at a level in the range of about 0.02 to about 0.15 ppm, more preferably about 0.025 to about 0.075 ppm.

In further inventive embodiments, a method of controlling aquatic weeds involves the use of a combination including bensulfuron-methyl and endothall. In such embodiments, the endothall can be used at a level in the range of about 0.1 to 3.5 ppm a.e., in certain embodiments at a level of less than about 1.4 ppm a.e., and typically at a level in the range of about 0.35 to about 1 ppm a.e., more preferably about 0.5 to about 1 ppm a.e.; and, the bensulfuron-methyl is used at a level less than about 0.5 ppm, and typically at a level in the range of about 0.01 to about 0.25 ppm, more preferably about 0.02 to about 0.1 ppm.

Any of the herbicides can be applied separately in liquid or solid form, or a combination product containing some or all herbicides could be produced, again, in either liquid or solid form. Typical liquid formulations include emulsions, suspensions (including suspensions containing microcapsules), solutions, emulsifiable concentrates, and flowables. Common solid forms include granules, wettable powders, water-dispersible solid (including water-dispersible granules containing microencapsulated pesticides) or dusts. The herbicidal formulation can also contain, in addition to the active herbicide(s) other ingredients such as solvents, wetting agents, suspending agents, anti-caking agents, dispersing agents, emulsifiers, antifreeze agents, antifoam agents, and other additives.

Compositions according to this invention may contain the two or more herbicides in numerous different physical forms. In some cases, a composition may be produced by simply physically mixing ("tank mixing") commercially available products containing the active herbicides. Alternatively, a package may be manufactured and sold which contains the two or more herbicides in separate containers, but packaged together, e.g. in a "multi-pack" format such as a "twin-pack" or "tri-pack".

Alternatively, previously prepared compositions ("premixes") containing the two or more herbicides can be produced. Suitable liquid compositions would include solutions or emulsions containing the two or more herbicides. A solid product containing the two or more herbicides could also be produced, for instance, as impregnated granules. When premixed or tank mixed herbicidal combinations are provided, they can include the penoxsulam or other ALS-inhibitor and endothall present in a ratio of about 1:2 to about 1:200 depending on the potency of the agent, respectively. In certain embodiments, premixed or tank mixed herbicidal combinations are provided that include penoxsulam and endothall present in a ratio of about 1:40 to about 1:700, respectively.

In use, the combination of herbicidal agents utilized should remain at herbicidal effective levels in the body of water and/or in contact with the targeted plant for sufficient time to achieve control. In accordance with certain preferred methods of the invention, at least one herbicidal agent level (e.g. ALS-inhibitor such as penoxsulam) will be maintained in the body of water and/or in contact with the plant for about one to four weeks, and in other preferred embodiments for at least about four weeks, sometimes in the range of about four to sixteen weeks or more. The other herbicidal agent (e.g. endothall) may or may not be present for the duration based on chemical half-lives in water or can be added to the other agent already in the presence of the target plant or vice versa; endothall will be present for at least about 1 day, and typically in the range of about 1 to 14 days or more. The concentration of any single herbicidal agent or both agents in the combination may be maintained, when necessary, with the target plant to ensure efficacy, for example, through the use of sequential or bump treatments, or continuous injection, using the same agent.

Bodies of water to be treated with the inventive methods will typically be fresh water bodies such as ponds, lakes, wet lands, reservoirs, rivers or irrigation canals, although other bodies of water may also be treated in accordance with the invention.

In order to promote a further understanding of the present invention and its various embodiments, the following specific examples are provided. It will be understood that these examples are illustrative and not limiting of the invention.

Example 1

Control of Hydrilla with Penoxsulam and Endothall—Field Study 1

This example demonstrates that penoxsulam used in combination with endothall provides surprisingly improved *hydrilla* control.

A 6 acre somewhat rectangular-shaped lake was divided into three 2 acre zones for this testing. A 2-acre test site (Zone 1), located on the northern one-third of the lake, was treated with a penoxsulam plus endothall combination in order to evaluate control of the exotic aquatic weed, *hydrilla* (*Hydrilla verticillata*). Within a 50 gallon spray tank system powered by a 5.5 Hp Honda motor, 0.523 gallons Galleon SC (a commercially available penoxsulam formulation) and 12.7 gallons Aquathol K (a commercially available endothall formulation) were added to 36.78 gallons of water. The herbicide combination mixture delivered an application dose of 15 parts per billion penoxsulam and 0.71 ppm a.e. endothall to Zone 1. This herbicide mixture was evenly injected using a trailing hose over the airboat bow throughout the 2 acre Zone 1. On the day of treatment, Zone 1 contained approximately 90% *hydrilla* coverage, with growth near or at the water surface.

The remaining 4 acres (both Zone 2 (central one-third) and Zone 3 (southern one-third)) of the lake were treated with 15 ppb penoxsulam alone on the same day. Both Zones 2 and 3 contained approximately 90-95% *hydrilla* coverage at that time.

Twenty one days following the initial treatment, the *hydrilla* was assessed for herbicidal injury within Zones 1, 2, and 3. Unexpectedly, *hydrilla* plants within Zone 1, (site which received the combination mixture treatment) were mostly necrotic, remaining stems were defoliated and most had lost integrity. Approximately 10% of the original plant volume remained near the water's surface; the balance had fallen to the lake bottom. The same was true for a 1 acre area contiguous down lake to Zone 1 moving into Zone 2. All remaining *hydrilla* plants suspended in the water column within the 3 acres were expressing severe injury.

Penoxsulam treated *hydrilla* typically requires about 60 days before severe injury is expressed and about 90 to 120 days or more before control is achieved. Endothall treatments are usually made with a 1.4 to 3.5 ppm a.e. dose and typically require 2-6 weeks before *hydrilla* plants defoliate and drop toward the lake bottom, dependent on plant maturity. A 0.71 ppm a.e. endothall partial area/spot treatment application generally would provide only slight *hydrilla* injury, such as limited defoliation or apical tip necrosis, yet essentially no *hydrilla* control. The *hydrilla* damage and control level found in Zone 1 were generally significantly greater and more rapid than a 21 day penoxsulam treatment at 150 ppb (maximum labeled rate) or a 3.5 ppm a.e. (maximum labeled rate) endothall treatment.

On the first evaluation date 21 days following the initial treatment, *hydrilla* in Zone 2 and Zone 3 expressed slight but expected penoxsulam injury. Approximately 90% *hydrilla* remained near the water's surface in Zone 3 and within the southern portion of Zone 2—no control was observed in these areas. On this date, 0.71 ppm a.e. endothall (12.7 gallons Aquathol K) was applied to Zone 3 in order to evaluate contact herbicidal efficacy 21 days following a penoxsulam treatment.

On the second evaluation date, sixty two days after the initial treatments, *hydrilla* in Zone 1 was 100% controlled with only necrotic stems present on the lake bottom. The control was present throughout the 3 acre area initially impacted (Zone 1 and northern ½ of Zone 2). Hydrilla in Zone 3 was also 100% controlled. Approximately 95% *hydrilla* control was observed in the southern half of Zone 2 (1 acre) and the plants present were displaying severe injury. Therefore, the northern 1 acre of Zone 2 was controlled by the original Zone 1 treatment and the southern portion 1 acre of Zone 2 was controlled by the intermediate treatment that occurred twenty one days after the initial treatment. At sixty two days, only a few severely damaged plants remained in the 6 acre lake.

On a third evaluation date, one hundred and three days after the initial treatments, no viable *hydrilla* could be found within the lake. Generally, at this time *hydrilla* would be expected to be recovering from an endothall alone treatment as being only a contact herbicide. Therefore, the combination of penoxsulam plus endothall provided faster control of *hydrilla* than expected from endothall or penoxsulam alone, and longer-term control than expected from endothall alone. This herbicide combination required a lower rate of each product than would have been required if each had been applied separately at normal use rates.

Example 2

Penoxsulam+Endothall Under Static Exposure to Hydrilla

This example demonstrates, at a minimum, an additive effect between an ALS-inhibitor and endothall, and also demonstrates this effect at reduced concentrations.

Materials and Methods

Single apical meristems of *hydrilla*, collected from Florida, were planted into small pots (13.5 cm length×3.75 cm diameter) containing Wallace Farm® topsoil amended with 14-14-14 slow release Osmocote® fertilizer (~2.5 g Osmocote/kg soil) on 18 Jul. 2008. Approximately 5 to 7 cm of the apical section extended above the sediment at planting, and a sand cap was placed over the potting soil (~2 cm deep). Plants were then transferred to a 12 L acrylic tanks filled with well water. Tanks were maintained in a growth room with 14:10 h photoperiod at 26° C. Plants were allowed to establish growth for 14 days before treatment.

Treatments were replicated three times in a completely randomized design. Treatments included: untreated controls; 100, 200, 400, 800, and 1600 ppb a.e. endothall; 10, 20, 40, 80, and 160 ppb penoxsulam; and 200, 400, and 800 ppb of combinations of penoxsulam+endothall at ratios of 1:39, 1:19, 1:9 and 1:4; additional concentrations of 100 ppb were included with 1:9 and 1:4 ratios. Treatments were under static conditions. Endothall was formulated as Aquathol K® (4.23 #/gallon dipotassium salt; or 3#/gallon a.e.); penoxsulam was formulated as Galleon SC® (2#/gallon active ingredient). All concentrations are expressed as a.e. for endothall.

All above ground biomass was harvested 55 days after treatment. Biomass was dried to constant moisture at 70° C., and dry weights were determined. Data were subjected to regression analysis using Sigma Plot software, and a $GR_{50}$ was determined (concentration causing a 50% reduction in dry weight). All data were analyzed for synergism/antagonism using the Isobole analysis at the 95% confidence level (estimated using linear interpolation from 95% confidence bands) (Berenbaum, M. C. 1989, Pharmacological Reviews. 41:93-141; Streibig, J. C. 2003, Assessment of herbicide effects: http://www.ewrs.org/et/images/, Herbicide interaction.pdf). This model is considered effective for determining synergism/antagonism without assuming that herbicides act independently when applied in combination (Green, J. M. and J. C. Streibig, 1993, Herbicide mixtures, Pages 117-134 in J. C. Streibig and P. Kudsk, eds. Herbicide Bioassays. Boca Raton, Fla.: CRC). The method assumes the efficacy of herbicides in combination is equal to efficacy of the singular agents unless there is synergism or antagonism (Armel, G. R., P. L. Rardon, M. C. McComrick and N. M. Ferry, 2007, Weed Tech., 21:947-953).

Results

Data were subjected to non-linear regression to calculate $GR_{50}$ values (FIG. 1). The $GR_{50}$ for penoxsulam alone was 12 ppb and endothall alone was 309 ppb (Table 1). The $GR_{50}$ for all ratios of penoxsulam and endothall combinations ranged from 57 to 295 ppb, and the values decreased with increasing ratios. As the penoxsulam concentration increased the associated endothall concentration decreased in combination (inverse correlation). For example, the penoxsulam component increased from 7 to 8 to 9 to 11 ppb and the endothall component declined from 288 to 149 to 84 to 46 ppb as the ratio increased from 1:39, 1:19, 1:9, to 1:4, respectively.

Figure 1A:
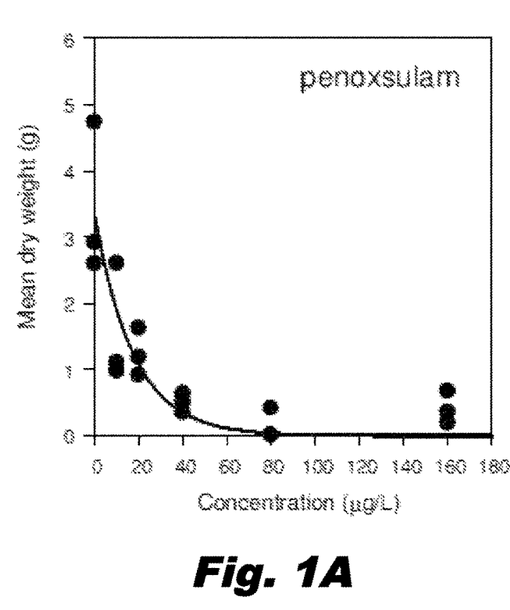
FIGS. 1A-1F display the response (biomass) of *hydrilla* to penoxsulam and endothall applied alone and in combination at various ratios.
Figure 1B:
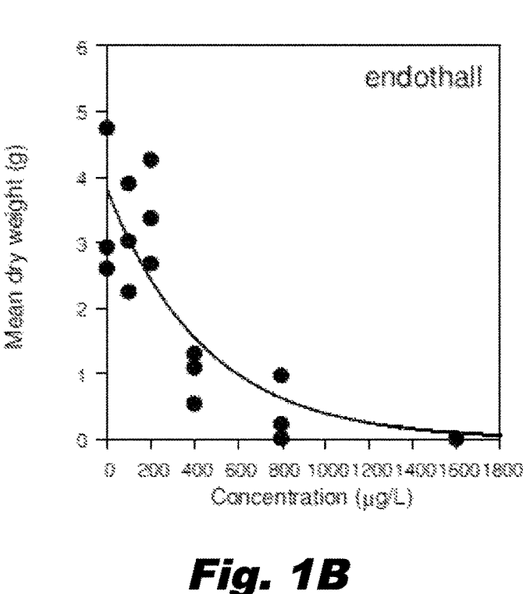
Figure 1C:
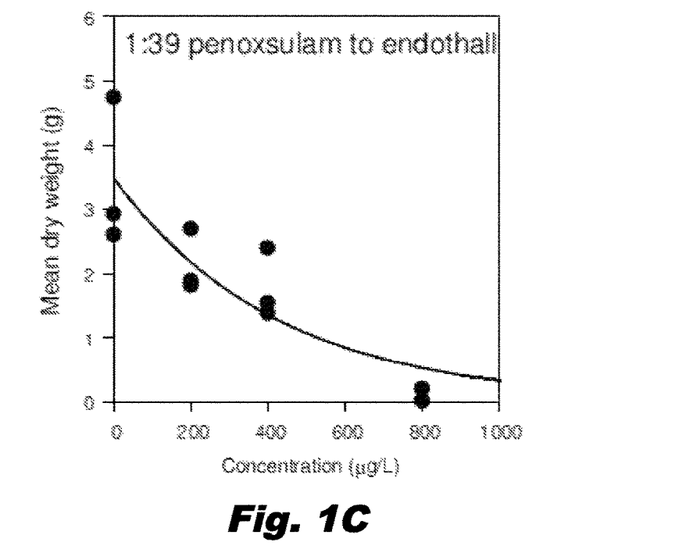
Figure 1D:
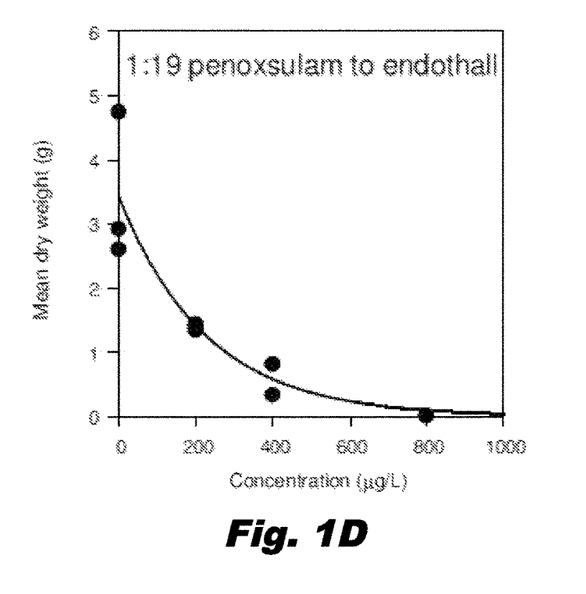
Figure 1E:
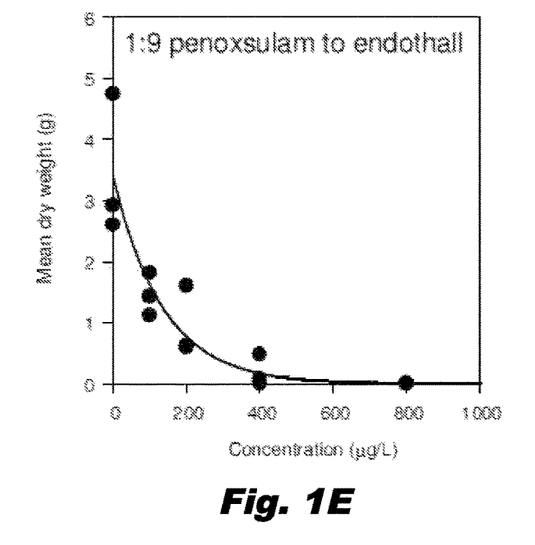
Figure 1F:
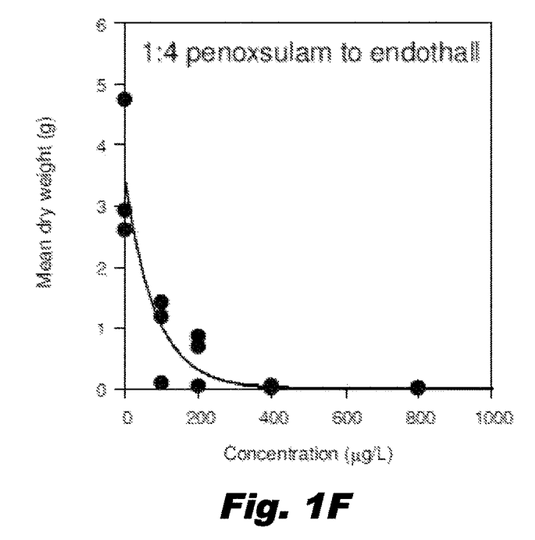
Figure 2:
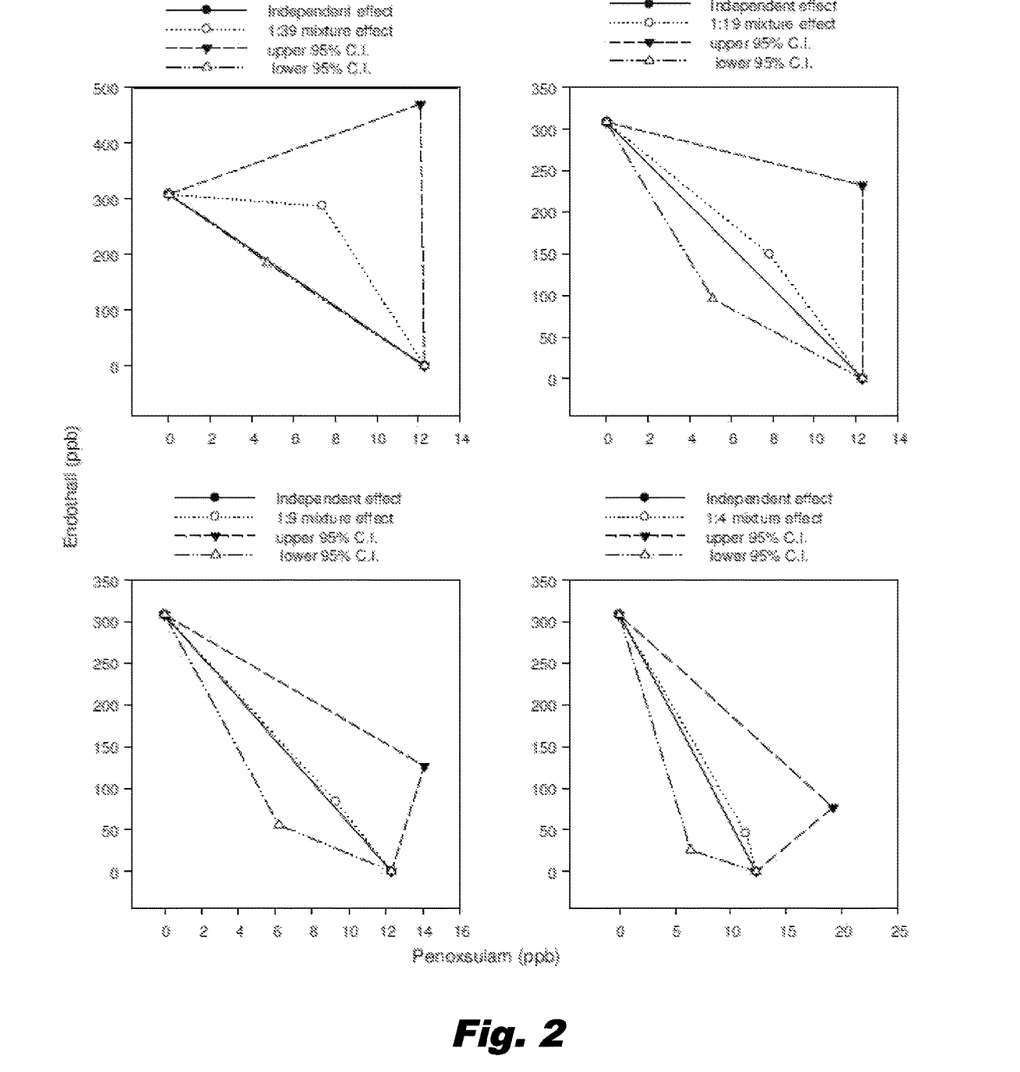
FIG. 2: Isobole analysis of penoxsulam and endothall mixtures on *hydrilla* (n=3). The "independent action" line defines the amount of each herbicide necessary to cause a 50% reduction in biomass assuming there is no antagonism/synergism. It was calculated based on the dose of penoxsulam or endothall each necessary to cause a 50% effect when applied alone. The action of the 2 herbicides in combination is synergistic if the mixture line falls below the independent action line. The action of the 2 herbicides is antagonistic if the mixture line is above the independent action line. When the mixture line falls between the upper and lower confidence intervals, this is indicative of an independent herbicidal response.

All ratios of penoxsulam to endothall resulted in an additive effect based on the Isobole analysis (FIG. 2). The endothall concentration necessary to elicit an additive response with penoxsulam was lowest in the 1:4 ratio (57 ppb). The endothall concentration necessary to cause a 50% reduction in biomass was lower in combination with penoxsulam at all ratios than when applied alone under static conditions.

TABLE 1

Calculated GR$_{50}$ values (ppb) for penoxsulam and endothall applied alone and at various ratios in combination to hydrilla under static exposure. Variance was estimated using linear interpolation from 95% confidence intervals (n = 3). The "penoxsulam ppb:endothall ppb" was calculated by multiplying the GR$_{50}$ value times the individual ratio for each herbicide.

| HERBICIDE | GR$_{50}$ (ppb) | 95% C.I. | Penoxsulam ppb: endothall ppb |
|---|---|---|---|
| Penoxsulam | 12 | 8 to 19 | n/a |
| Endothall | 309 | 202 to 498 | n/a |
| 1:39 penoxsulam:endothall | 295 | 190 to 483 | 7:288 |
| 1:19 penoxsulam:endothall | 157 | 102 to 246 | 8:149 |
| 1:9 penoxsulam:endothall | 93 | 62 to 141 | 9:84 |
| 1:4 penoxsulam:endothall | 57 | 32 to 96 | 11:46 |

Positive interaction between endothall and penoxsulam was not expected. There was potential for antagonism. Endothall requires shorter exposure than penoxsulam; endothall is a contact herbicide whereas penoxsulam is a systemic herbicide. Penoxsulam is an ALS-inhibitor that requires a sustained exposure (60 to 120+ days) with submersed plants to achieve effective systemic control (SePRO Corporation, 2009, Galleon SC® Specimen Label, 11550 N. Meridian St., Suite 600, Carmel, Ind. 46032). It is active at relatively low concentrations, requiring concentrations from about 0.01 to 0.15 ppm, depending on the exposure. Endothall is a relatively rapid acting contact herbicide that requires generally less than 72 hours of contact with *hydrilla* to achieve effective control (Netherland, M. D., W. R. Green and K. D. Getsinger. 1991. J. Aquatic Plant Manage. 29: 61-67). Although the exact mechanism of action is unknown, it is believed to be an uncoupler of membrane transport systems (MacDonald. G. E., R. Querns, D. G. Shilling, T. A. Bewick and S. K. McDonald. 2003. J. Aquatic Plant Manage. 42: 13-18). Concentrations generally range from about 1.4 to 3.5 ppm a.e. (Cerexagri Inc., 2007, Aquathol K® Specimen Label, 630 Freedom Business Center, Suite 403, King of Prussia, Pa. 19406). Endothall injures susceptible plants relatively quickly with resultant loss in cell integrity, which could inhibit or preclude effective translocation of a systemic herbicide such as penoxsulam. However, antagonistic activity was not observed with simultaneous treatment in this experiment, demonstrating that the agents can be effectively used together without inhibiting the activity of either agent.

Example 3

Penoxsulam+Endothall Under Multiple Exposures to Hydrilla

This example demonstrates that an ALS-inhibitor in combination with endothall can result in reduced exposure times, and sequencing can influence the interaction.

Materials and Methods

Apical sections (12 to 15 cm in length) of *hydrilla*, collected from Florida, were planted into small pots (13.5 cm length×3.75 cm diameter) containing Wallace Farm® topsoil amended with 14-14-14 slow release Osmocote® fertilizer (~2.5 g Osmocote/kg soil) on 16 Oct. 2008. Approximately 5 to 7 cm of the apical section extended above the sediment at planting, and a sand cap was placed over the potting soil (~2 cm deep). Plants were then transferred to a 12 L acrylic tanks filled with well water. Tanks were maintained in a growth room with 14:10 h photoperiod at 26° C. Plants were allowed to grow for 8 days before the following treatments were initiated in triple replicate:
A) Untreated controls
B) Penoxsulam at 0.02 mg/L
C) Endothall at 0.68 mg/L a.e.
D) Simultaneous treatment
  a. Penoxsulam 0.02 mg/L+endothall at 0.68 mg/L
    i. Exposure times
      1. 3 days
      2. 6 days
      3. 12 days
      4. 24 days
      5. 48 days (static)
E) Sequential treatment
  a. Penoxsulam 0.02 mg/L, add 0.68 mg/L endothall 24 days later—static exposure to combination
  b. Endothall at 0.68 mg/L, add 0.02 mg/L penoxsulam 24 days later—static exposure to combination
  c. Penoxsulam 0.02 mg/L, add 0.68 mg/L endothall 12 days later—12 day exposure to combination
  d. Endothall at 0.68 mg/L, add 0.02 mg/L penoxsulam 12 days later—12 day exposure to combination
  e. Penoxsulam 0.02 mg/L, add 0.68 mg/L endothall 6 days later—6 day exposure to combination
  f. Endothall at 0.68 mg/L, add 0.02 mg/L penoxsulam 6 days later—6 day exposure to combination Endothall was formulated as Aquathol K® (4.23 #/gallon dipotassium salt, or 3#/gallon a.e.); penoxsulam was formulated as Galleon SC® (2#/gallon active ingredient). All concentrations are expressed as a.e. for endothall. At each exposure time, plants were removed from treatments and placed in a tank with fresh water containing no herbicide (including controls) to remove the aqueous exposure and allow for recovery.

Plants were harvested at 48 days after initial treatment. At harvest, plants were rinsed free of algae and placed in paper sacks in a drying oven for 4 days at 70° C. temperature. Mean dry weights were determined and means separated using least significant differences. Difference between observed and expected responses was determined to evaluate potential interactions using methods reported by Colby (Colby S. R. 1967. Weeds. 15:20-22).

Results

Biomass data is presented in Table 2. Penoxsulam had greater activity on *hydrilla* as exposures increased, but not significantly different from untreated controls. This was partially expected as penoxsulam generally requires 60 to 120 days or longer to control submersed aquatic plants (SePRO Corporation 2009, supra). Although exposures were maintained for up to 48-days with penoxsulam, endothall likely did not remain at herbicidal levels due to its shorter half-life in water and mechanism of breakdown (microbial). Endothall reduced *hydrilla* biomass compared to untreated controls at all exposure periods, except 3 and 6-day. Treatments with combinations of endothall+penoxsulam were significantly different from either herbicide alone following 12 and 24 day exposure with a simultaneous treatment and endothall followed-by penoxsulam in 12-day exposure. Combination treatments generally resulted in greater effect than from either herbicide alone except for when penoxsulam was followed-by an endothall exposure.

Simultaneous treatments of penoxsulam+endothall (3, 6, 24 and 48 day exposures) and the sequence of penoxsulam following 6, 12, or 24 days of an endothall treatment resulted in synergistic activity based on analyses of interactions (Table 3). The sequencing of penoxsulam followed-by endothall resulted in an antagonistic effect. Thus, the combination of penoxsulam+endothall could result in antagonism or synergism based on sequencing. This seems counterintuitive: the effectiveness of a contact herbicide was minimized if plants were predisposed to a sub-lethal exposure to an ALS-inhibitor/systemic herbicide; that same ALS-inhibiting herbicide was more effective after plants were predisposed to that same membrane disruptor/contact herbicide. As observed in example 1, penoxsulam followed-by endothall can be an effective combination. Thus, the effectiveness of an ALS-inhibitor followed-by endothall seems influenced by sequence timing more than endothall followed-by an ALS-inhibitor.

Considering the reduced exposure times in this study compared to those required with penoxsulam alone, these data indicated a synergy between combinations of penoxsulam plus endothall, and sequencing was important. Simultaneous application or endothall followed-by penoxsulam resulted in positive interaction, whereas penoxsulam followed-by endothall resulted in negative interaction. The addition of endothall to penoxsulam resulted in significantly reduced exposure requirements compared to penoxsulam alone. The addition of penoxsulam to endothall resulted in positive interaction on *hydrilla* regardless of the exposure time evaluated at the concentrations tested, and at reduced endothall concentrations.

Coupled with the results of Example 2 (static conditions) there was, at a minimum, an additive effect between an ALS-inhibitor (penoxsulam) and endothall. With various exposure times (3, 6, 12, 24, and 48 d), analyses indicated synergism between an ALS-inhibitor (penoxsulam) and endothall. Applying endothall in combination with an ALS-inhibitor, such as penoxsulam, appeared to reduce the exposure requirement necessary with an ALS-inhibitor to achieve systemic control, with lower concentrations of endothall than required when used singularly.

TABLE 2

Mean dry weight of hydrilla (n = 3) following various exposures to combinations of endothall and penoxsulam in simultaneous combination or in sequencing (e.g. endothall followed-by (f/b) penoxsulam). Means followed by different letter are significantly different at $p = 0.05$ according to least significant difference (LSD).

| TREATMENT (mg/L a.e.) | 3-d | 6-d | 12-d | 24-d | 48-d |
|---|---|---|---|---|---|
| CONTROL | 3.48ab | 4.20a | 3.81a | 4.53a | 4.63a |
| PENOXSULAM (0.02) | 4.01a | 3.97a | 3.68ab | 3.24ab | 2.41ab |
| ENDOTHALL (0.68) | 2.24b | 2.61ab | 2.72c | 2.14bc | 1.62b |
| PENOXSULAM + ENDOTHALL (0.02 + 0.68) | 2.06b | 1.15b | 1.83d | 0.11d | 0.39b |
| ENDOTHALL f/b PENOXSULAM (0.68 + 0.02) | — | 1.28b | 0e | 0.73cd | — |
| PENOXSULAM f/b ENDOTHALL (0.02 + 0.68) | — | 2.04b | 2.87bc | 1.61bcd | — |
| (LSD) | 1.70 | 1.62 | 0.83 | 1.79 | 2.92 |

TABLE 3

Assessment of the interaction between endothall and penoxsulam using methods reported by Colby (1967). All data presented as a percent of control.

| TREATMENT | EXPSOURE (days) | OBSERVED RESPONSE | EXPECTED RESPONSE | DIFFERENCE IN RESPONSE[1] |
|---|---|---|---|---|
| PENOXSULAM (0.02) | 3 | 115 | — | — |
| ENDOTHALL (0.68) | 3 | 64 | — | — |
| PENOXSULAM + ENDOTHALL (0.02 + 0.68) | 3 | 59 | 74 | +15 |
| PENOXSULAM (0.02) | 6 | 95 | — | — |
| ENDOTHALL (0.68) | 6 | 62 | — | — |
| PENOXSULAM + ENDOTHALL (0.02 + 0.68) | 6 | 27 | 59 | +32 |
| ENDOTHALL f/b PENOXSULAM (0.68 + 0.02) | 6 | 30 | 59 | +29 |
| PENOXSULAM f/b ENDOTHALL (0.02 + 0.68) | 6 | 49 | 59 | +10 |
| PENOXSULAM (0.02) | 12 | 97 | — | — |
| ENDOTHALL (0.68) | 12 | 48 | — | — |
| PENOXSULAM + ENDOTHALL (0.02 + 0.68) | 12 | 48 | 47 | −1 |
| ENDOTHALL f/b PENOXSULAM (0.68 + 0.02) | 12 | 0 | 47 | +47 |
| PENOXSULAM f/b ENDOTHALL (0.02 + 0.68) | 12 | 75 | 47 | −28 |
| PENOXSULAM (0.02) | 24 | 72 | — | — |
| ENDOTHALL (0.68) | 24 | 47 | — | — |
| PENOXSULAM + ENDOTHALL (0.02 + 0.68) | 24 | 2 | 34 | +32 |
| ENDOTHALL f/b PENOXSULAM (0.68 + 0.02) | 24 | 16 | 34 | +18 |
| PENOXSULAM f/b ENDOTHALL (0.02 + 0.68) | 24 | 36 | 34 | −2 |
| PENOXSULAM (0.02) | 48 | 52 | — | — |

TABLE 3-continued

Assessment of the interaction between endothall and penoxsulam using methods reported by Colby (1967). All data presented as a percent of control.

| TREATMENT | EXPSOURE (days) | OBSERVED RESPONSE | EXPECTED RESPONSE | DIFFERENCE IN RESPONSE[1] |
|---|---|---|---|---|
| ENDOTHALL (0.68) | 48 | 35 | — | — |
| PENOXSULAM + ENDOTHALL (0.02 + 0.68) | 48 | 8 | 18 | +10 |

[1]Calculated as difference between observed and expected values.
A positive number indicates synergism; a negative number indicates potential antagonism.

Example 4

Penoxsulam+Endothall Field Study 2

Materials and Methods

A 15.2 acre lake, with an average depth of 11.9 feet (Polk County, Fla.) was treated on Feb. 10, 2009 with a targeted dose of 0.02 ppm penoxsulam (Galleon SC®) and 0.71 ppm endothall (Aquathol K®). The submersed plant community was dominated by *hydrilla*. The efficacy of the treatment on the submersed plant community was assessed by conducting hydroacoustic transects using georeferenced echosounder data (water depth, percent of bottom covered in vegetation (biocover) and the height of plants in the water column). Based on these values, plant biovolume was calculated, which is a combination of biocover and height information that estimates the percentage of the water column occupied by submersed vegetation at any given point. Hydrilla efficacy was also assessed by collecting biomass of *hydrilla* before herbicide impact and then 28 days after treatment. Biomass was collected from 5 to 6 random sites within a spatial area identified pre-treatment with relatively uniform *hydrilla* growth. Water temperature and dissolved oxygen were also measured.

Results

Figure 3:
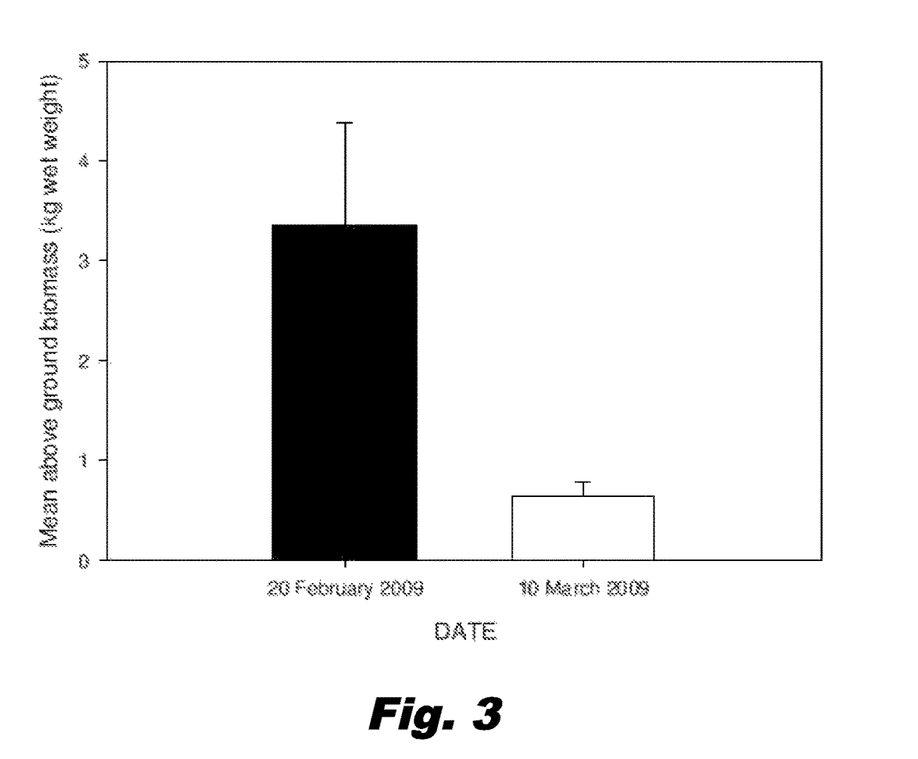
FIG. 3: Mean *hydrilla* biomass from a lake FL treated with a combination of penoxsulam (0.02 ppm) and endothall (0.71 ppm) on 10 Feb. 2009 (n=5 on 20 February; n=6 on 10 March).

Hydroacoustic data indicated the biovolume of submersed plants decreased by 85% by 28 days after treatment (Table 4). The submersed plant community largely consisted of *hydrilla*. The hydroacoustic data was similar to *hydrilla* biomass collected which indicated an 81% decrease on 10 Mar. 2009 (FIG. 3). Dissolved oxygen levels can be negatively affected by rapid reductions in submersed plant biomass, but dissolved oxygen levels were maintained above critical levels following treatment with penoxsulam+endothall (Table 5).

Endothall is generally applied at approximately 2.1 ppm a.e. (labeled concentrations of 1.4 to 2.8 ppm a.e.) depending on the site (Cerexagri 2007, supra), and penoxsulam generally needs to be maintained for 60 to 120 days or longer (SePRO Corporation 2009, supra). In combination, unexpectedly these data indicated that a reduced concentration of endothall and a reduced exposure to penoxsulam can be effective on *hydrilla*.

TABLE 4

Changes in the biovolume of submersed plants (i.e. hydrilla) following treatment with the combination of penoxsulam + endothall (DAT - days after treatment).

|  | 29 Jan. 2009 | 24 Feb. 2009 | 10 Mar. 2009 |
|---|---|---|---|
| DAT | PRETREATMENT | 14 | 28 |
| Biovolume | 44% | 12% | 6.5% |
| Percent reduction | — | 73% | 85% |

TABLE 5

Water temperature (Celsius) (TEMP) and dissolved oxygen (mg/L) (D.O.) profiles following treatment with penoxsulam + endothall in a lake dominated by hydrilla (submersed plant biovolume of 44% and biocover of 53%).

| | 9 Feb. 2009 14:00 hours | | 17 Feb. 2009 11:50 hours | | 24 Feb. 2009 13:15 hours | | 27 Feb. 2009 07:00 hours | | 3 Mar. 2009 09:00 hours | | 10 Mar. 2009 10:15 hours | |
|---|---|---|---|---|---|---|---|---|---|---|---|---|
| FEET | TEMP | DO | TEMP | DO | TEMP | DO | TEMP | DO | TEMP | DO | TEMP | DO |
| 1 | 16.6 | 8.5 | 18.9 | 6.9 | 18.8 | 6.5 | 18.7 | 6.8 | 17.7 | 5.7 | 21.7 | 6.6 |
| 2 | 16.6 | 8.5 | 18.9 | 6.5 | 18.7 | 6.5 | 18.6 | 6.6 | 17.7 | 5.7 | 21.5 | 6.7 |
| 3 | 16.5 | 8.0 | 18.9 | 6.9 | 18.6 | 6.2 | 18.6 | 6.5 | 17.7 | 5.5 | 21.4 | 6.0 |
| 4 | 16.4 | 8.0 | 18.8 | 6.9 | 18.4 | 6.2 | 18.6 | 6.5 | 17.7 | 5.6 | 21.2 | 6.3 |
| 5 | 15.2 | 7.3 | 18.8 | 6.9 | 18.2 | 6.0 | 18.6 | 6.5 | 17.7 | 5.6 | 20.5 | 5.1 |
| 6 | 15.1 | 7.3 | 18.5 | 6.5 | 18.1 | 6.0 | 18.6 | 6.5 | 17.7 | 5.6 | 19.9 | 5.8 |
| 7 | 15.1 | 7.3 | 18.2 | 6.2 | 18.0 | 5.7 | 18.6 | 6.3 | 17.7 | 5.6 | 19.3 | 6.7 |
| 8 | 15.0 | 7.3 | 16.9 | 6.5 | 17.9 | 5.8 | 18.6 | 6.3 | 17.7 | 5.6 | 18.8 | 6.5 |
| 9 | 14.9 | 7.3 | 16.5 | 6.6 | 17.8 | 6.3 | 18.3 | 5.4 | 17.7 | 5.6 | 18.6 | 5.8 |
| 10 | — | — | 16.5 | 6.6 | 17.7 | 6.0 | 18.2 | 5.2 | 17.7 | 5.6 | 18.4 | 5.5 |
| 11 | — | — | 16.5 | 6.6 | 17.7 | 6.0 | 18.0 | 5.0 | 17.7 | 5.6 | 18.2 | 4.4 |
| 12 | — | — | 15.7 | 5.5 | 17.6 | 5.0 | 17.7 | 4.0 | 17.7 | 5.6 | 18.1 | 3.7 |

TABLE 5-continued

Water temperature (Celsius) (TEMP) and dissolved oxygen (mg/L) (D.O.) profiles
following treatment with penoxsulam + endothall in a lake dominated by
hydrilla (submersed plant biovolume of 44% and biocover of 53%).

| | 9 Feb. 2009 14:00 hours | | 17 Feb. 2009 11:50 hours | | 24 Feb. 2009 13:15 hours | | 27 Feb. 2009 07:00 hours | | 3 Mar. 2009 09:00 hours | | 10 Mar. 2009 10:15 hours | |
|---|---|---|---|---|---|---|---|---|---|---|---|---|
| FEET | TEMP | DO | TEMP | DO | TEMP | DO | TEMP | DO | TEMP | DO | TEMP | DO |
| 13 | — | — | — | — | 16.7 | 3.1 | 17.4 | 3.0 | 17.7 | 5.6 | 18.0 | 3.4 |
| 14 | — | — | — | — | 16.5 | 3.0 | 17.3 | 3.0 | — | — | — | — |

Example 5

Imazamox+Endothall Under Static Exposure to Hydrilla

This example demonstrates that the ratio of an ALS-inhibitor in combination with endothall can influence interaction.

Materials and Methods

Single apical meristems of *hydrilla*, collected from Florida, were planted into small pots (13.5 cm length×3.75 cm diameter) containing Wallace Farm® topsoil amended with 14-14-14 slow release Osmocote® fertilizer (~2.5 g Osmocote/kg soil) on 4 November 2008. Approximately 5 to 7 cm of the apical section extended above the sediment at planting, and a sand cap was placed over the potting soil (~2 cm deep). Plants were then transferred to a 12 L acrylic tanks filled with well water. Tanks were maintained in a growth room with 14:10 h photoperiod at 26° C. Plants were allowed to establish growth for 10 days before treatment.

Treatments were replicated three times in a completely randomized design. Treatments included: untreated controls; 100, 200, 400, 600, and 800 ppb a.e. endothall; 25, 50, 100, 200, and 400 ppb imazamox; and 200, 400, 600 and 800 ppb of combinations of endothall plus imazamox at ratios of 19:1, 9:1, and 5.7:1. Treatments were under static conditions. Endothall was formulated as Aquathol K® (4.23 #/gallon dipotassium salt, or 3#/gallon a.e.); imazamox was formulated as Raptor® (1#/gallon active ingredient). All concentrations are expressed as a.e. for endothall.

All above ground biomass was harvested 34 days after treatment. Biomass was dried to constant moisture at 70° C., and dry weights were determined. Data were subjected to regression analysis using Sigma Plot software, and a $GR_{50}$ was determined (concentration causing a 50% reduction in dry weight). All data were analyzed for synergism/antagonism using the Isobole analysis at the 95% confidence level (estimated using linear interpolation from 95% confidence bands) (refer to Example 2 for more information on Isobole analysis).

Results

Figure 4:
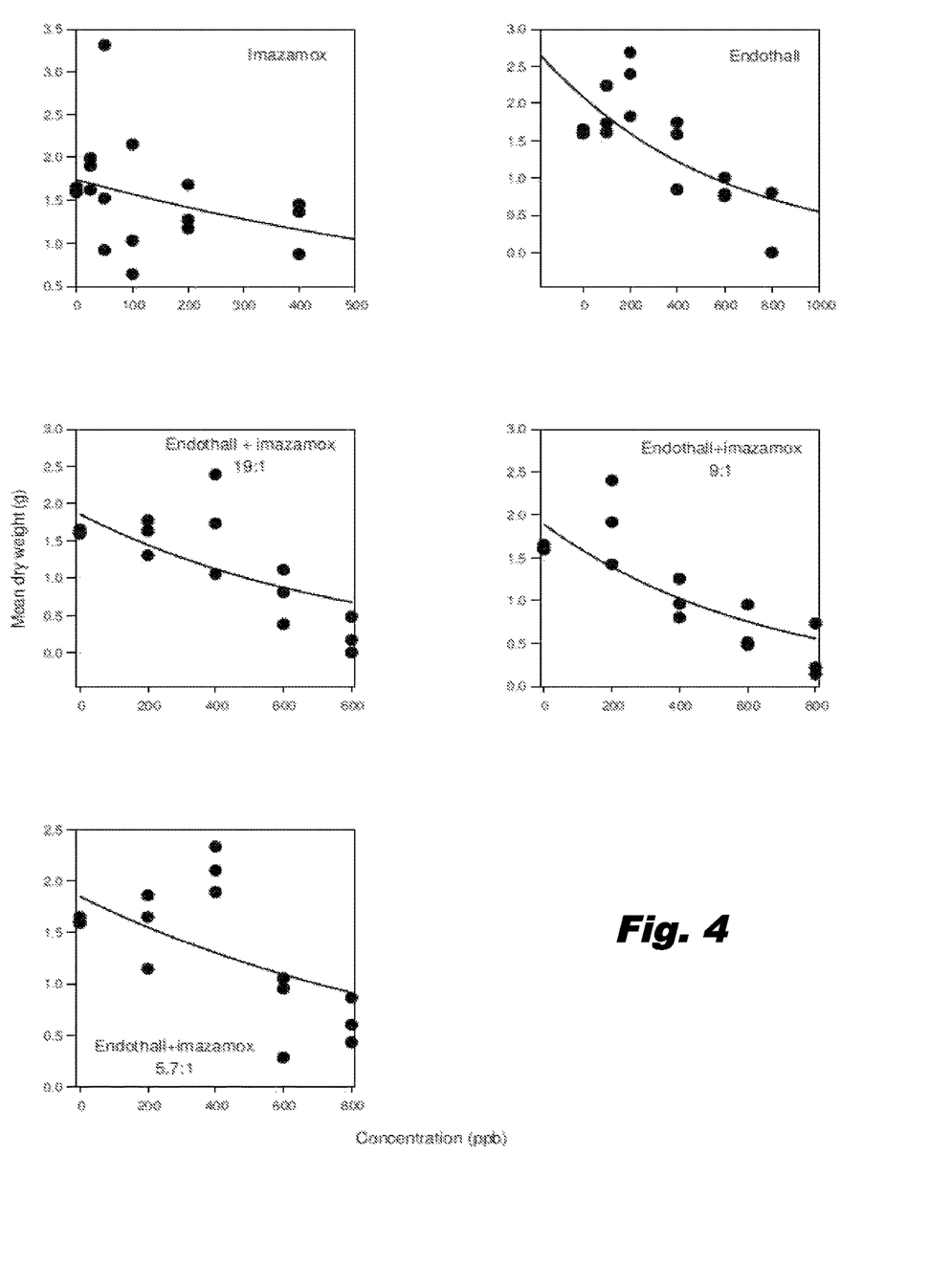
FIG. 4 displays the response (biomass) of *hydrilla* to imazamox and endothall applied alone and in combination at various ratios.
Figure 5:
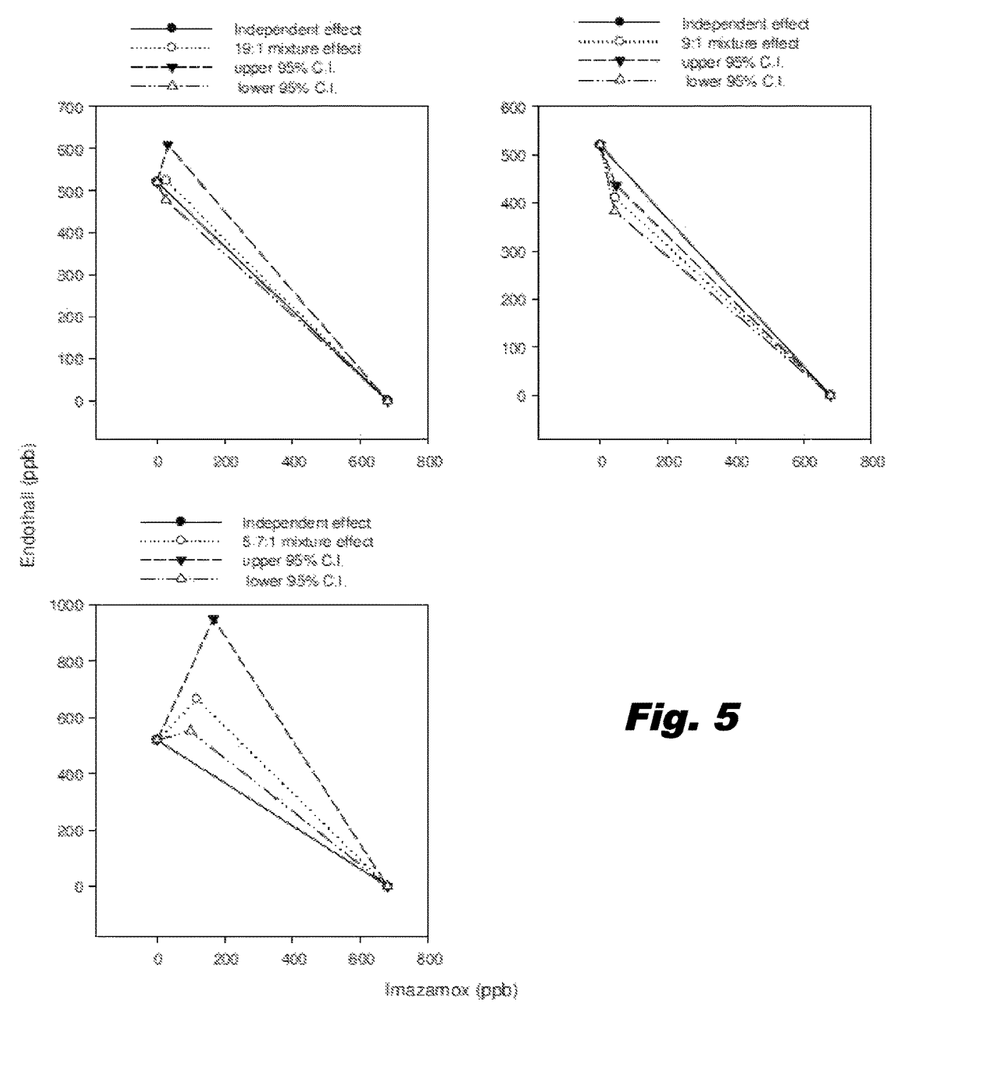
FIG. 5: Isobole analysis of imazamox and endothall mixtures on *hydrilla* (n=3). The "independent action" line defines the amount of each herbicide necessary to cause a 50% reduction in biomass assuming there is no antagonism/synergism. It was calculated based on the dose of imazamox or endothall each necessary to cause a 50% effect when applied alone. The action of the 2 herbicides in combination is synergistic if the mixture line falls below the independent action line. The action of the 2 herbicides is antagonistic if the mixture line is above the independent action line. When the mixture line falls between the upper and lower confidence intervals, this is indicative of an independent herbicidal response.

Data were subjected to non-linear regression to calculate $GR_{50}$ values (FIG. 4). The $GR_{50}$ for imazamox alone was 680 ppb and endothall alone was 520 ppb (Table 6). The $GR_{50}$ for all ratios of penoxsulam and endothall combinations ranged from 455 to 784 ppb. Depending on the ratio of endothall to imazamox, various interactions occurred ranging from antagonism to synergism based on the Isobole analysis (FIG. 5). A ratio of 19:1 resulted in an additive effect, 9:1 resulted in synergy, and 5.7:1 resulted in antagonism. Thus, the ratio of endothall:imazamox was critical to enhancing efficacy when applied in combination to reduce exposure requirements or reduce concentrations of at least one of the agents in the mixture.

TABLE 6

Calculated $GR_{50}$ values (ppb) for imazamox and endothall applied
alone and at various ratios in combination to hydrilla under static.
Variance was estimated using linear interpolation from 95% confidence
intervals (n = 3). The "endothall ppb:imazamox ppb" was calculated
by multiplying the $GR_{50}$ value times the individual ratio for
each herbicide.

| HERBICIDE | $GR_{50}$ (ppb) | 95% C.I. | Endothall ppb: imazamox ppb |
|---|---|---|---|
| Imazamox | 680 | 355 to 1751 | n/a |
| Endothall | 520 | 467 to 679 | n/a |
| 19:1 endothall:imazamox | 551 | 503 to 641 | 523:28 |
| 9:1 endothall:imazamox | 455 | 426 to 484 | 410:46 |
| 5.7:1 endothall:imazamox | 784 | 651 to 1118 | 666:118 |

The uses of the terms "a" and "an" and "the" and similar references in the context of describing the invention (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected. In addition, all references cited herein are indicative of the level of skill in the art and are hereby incorporated by reference in their entirety.

What is claimed is:

1. A method for controlling *hydrilla* in a body of fresh water, comprising:
   providing in the body of fresh water a synergistically effective amount of a herbicidal combination including an ALS-inhibiting herbicide and endothall, so as to control the *hydrilla*, wherein the ALS-inhibiting herbicide is penoxsulam, imazamox, or bispyribac sodium;

wherein said providing comprises adding the endothall to the body of fresh water prior to or simultaneously with adding the ALS-inhibiting herbicide to the body of fresh water;

wherein said providing comprises providing the endothall at a level of about 0.1 to about 3.5 ppm in the body of fresh water; and with the further proviso that:
(i) where the ALS-inhibiting herbicide is penoxsulam, the penoxsulam is applied to the body of fresh water to provide a penoxsulam level of about 2.5 to 50 ppb in the body of fresh water;
(ii) where the ALS-inhibiting herbicide is imazamox, the imazamox is applied to the body of fresh water to provide an imazamox level of about 0.02 to about 0.15 ppm in the body of fresh water; and
(iii) where the ALS-inhibiting herbicide is bispyribac sodium, the bispyribac sodium is applied to the body of fresh water to provide a bispyribac sodium level of about 0.01 to about 0.25 ppm in the body of fresh water.

2. The method of claim 1, wherein said providing comprises providing the endothall at a level of about 1.4 ppm or less in the body of fresh water.

3. The method of claim 2, wherein the ALS-inhibiting herbicide is penoxsulam.

4. The method of claim 2, wherein the ALS-inhibiting herbicide is imazamox.

5. The method of claim 2, wherein the ALS-inhibiting herbicide is bispyribac sodium.

6. The method of claim 1, wherein the ALS-inhibiting herbicide is imazamox.

7. The method of claim 1, wherein the ALS-inhibiting herbicide is penoxsulam.

8. The method of claim 1, wherein the ALS-inhibiting herbicide is bispyribac sodium.

9. The method of claim 1, wherein said providing comprises adding the endothall to the body of fresh water simultaneously with the ALS-inhibiting herbicide.

10. The method of claim 9, wherein the ALS-inhibiting herbicide comprises penoxsulam.

11. The method of claim 9, wherein the ALS-inhibiting herbicide comprises imazamox.

12. The method of claim 9, wherein the ALS-inhibiting herbicide comprises bispyribac sodium.

13. The method of claim 9, wherein said providing comprises adding the endothall to the body of fresh water separately from the ALS-inhibiting herbicide.

14. The method of claim 9, wherein said providing comprises adding the endothall to the body of fresh water in a combined product with the ALS-inhibiting herbicide.

15. The method of claim 1, wherein the body of fresh water is a pond, lake, wet land, reservoir, river or irrigation canal.

* * * * *